United States Patent [19]
Elliott et al.

[11] Patent Number: 5,478,556
[45] Date of Patent: Dec. 26, 1995

[54] VACCINATION OF CANCER PATIENTS USING TUMOR-ASSOCIATED ANTIGENS MIXED WITH INTERLEUKIN-2 AND GRANULOCYTE-MACROPHAGE COLONY STIMULATING FACTOR

[76] Inventors: Robert L. Elliott, 17310 Masters Pointe Ct., Baton Rouge, La. 70810; Jonathan F. Head, 6144 Hagerstown Dr., Baton Rouge, La. 70817

[21] Appl. No.: 202,516

[22] Filed: Feb. 28, 1994

[51] Int. Cl.$^6$ .......................... A61K 45/05; A61K 39/00; C07K 14/535; C07K 14/55
[52] U.S. Cl. .................. 424/85.2; 424/85.1; 424/277.1; 530/351; 530/828
[58] Field of Search .................. 424/277.1, 85.1, 424/85.2; 530/828, 351

[56] References Cited

U.S. PATENT DOCUMENTS

| Re. 33,071 | 9/1989 | Stjernholm | 530/394 |
|---|---|---|---|
| 5,208,323 | 5/1993 | Page et al. | 530/391.9 |

FOREIGN PATENT DOCUMENTS 9306867  4/1993  WIPO.

OTHER PUBLICATIONS

Bystryn J. C., Cancer & Metastasis Rev. 9:81–91, 1990.
Colombo et al, Immunology Today 12(7): 249–250, 1991.
Brandes et al, Cancer Res 52(13): 3796–3800, 1992.
Kohn et al, Int. J. Cancer 53:968–972, 1993.
Martensson et al, Toxic in Vitro 7(3):241–245, 1993.
Hellström et al, Ann. N.Y. Acad Sci 690:24–33, 1993.
Berd et al, Cancer Res 46(5) 2572–2577, 1986.
Cassel W. A., Murray D.R., Phillips H. S., "A Phase II Study on the Postsurgical Management of Stage II Malignant Melanoma with a Newcastle Disease Virus Oncolysate," *Cancer* 52:856–860, 1983.
Humphrey L. J., Taschler–Collins S., Goldfarb P. M., et al., "Adjuvant Immunotherapy for Melanoma," *J. Surg. Oncol.* 25:303–305, 1984.
Hoover H. C., Surdyke M. G., Dangel R. B., et al., "Prospectively Randomized Trial of Adjuvant Active Specific Immunotherapy for Human Colorectal Cancer," *Cancer* 55:1256–1243, 1985.
Morton D. L., "Adjuvant Immunotherapy of Malignant Melanoma: Status of Clinical Trials at UCLA," *Int. J. Immunotherapy* II(1):31–38, 1986.
Hersey P., Edwards A., Coates A., et al., "Evidence that treatment with vaccinia melanoma cell lysates (vmcl) may improve survival of patients with stage II melanoma," *Cancer Immunol. Immunotherapy* 25:257–265, 1987.
Mitchell M. S., Harel W., Kempf R. A., et al., "Active–Specific Immunotherapy for Melanoma," *J. Clin. Oncol.* 8:856–869, 1990.
Wallack M. K., Bash J., and Bartolucci A., "Improvement in Disease–free Survial of Melanoma Patients in Conjuction With Serologic Response in a Phase Ia/Ib Southeastern Cancer Study Group Trial of Vaccinia Melanoma Oncolysate," *Am. Surg.*, 55:243–247, 1989.
Morton D. L., Nizze A., Famatiga E., et al., "Clinical Results of a Trial of Active Specific Immunotherapy With Melanoma Cell Vaccine and Immunomodulation in Metastatic Melanoma," *Proc. Am. Assoc. Cancer Res.* 30:383, 1989.
Hollinshead A., Stewart T. H. M., Takita H., et al., "Adjuvant Specific Active Lung Cancer Immunotherapy Trials," *Cancer*, 60:1249–1262, 1987.
Wiseman C., Rao S., Kennedy P., et al., "Clinical Responses In Autologous Active Specific Intralymphatic Immunotherapy (AASILI) Correlate With Augmentation Of CD4+ Peripheral Blood Lymphocytes (PBL)," *Proc. Am. Soc. Clin. Oncol.* 8:186 1989.
Livingston P., "Active Specific Immunotherapy in the Treatment of Patients with Cancer," *Human Cancer Immunology* II:401–423, 1991.
Dean J. H., McCoy J. L., Cannon G. B., et al., "Cell–Mediated Immune Responses of Breast Cancer Patients to Autologous Tumor–Associated Antigens," *J. Nat'l Cancer Inst.* 58:549–555 1977.
Flaherty L. E., Redman B. G., Chabot G. G., et al. "A Phase I–II Study of Dacarbazine in Combination With Outpatient Interleukin–2 in Metastatic Malignant Melanoma", *Cancer* 65:2471–2477, 1990.
Gianni A. M., Bregni M., Siena S., et al., "Recombinant Human Granulocyte–Macrophage Colony–Stimulating Factor Reduces Hematologic Toxicity and Widens Clinical Applicability of Hight–Dose Cyclophosphamide Treatment in Breast Cancer and Non–Hodgkin's Lymphoma," *J. Clin, Oncol.* 8:768–778, 1990.
Atzpodien J. and Kirchner H., "The Out–Patient Use of recombinant Human Interleukin–2 and Interferon Alfa–2b in Advanced Malignancies", *Eur. J. Cancer* 27:588–592, 1991.
Caligiuri, M. A., Murray C., Soiffer R. J., et al. "Extended Continuous Infusion Low–Dose Recombinant Interleukin–2 in Advanced Cancer: Prolonged Immunomodulation Without Significant Toxicity," *J. Clin. Oncol.* 9:2110–2119, 1991.
Figlin R. A., Belldegrun A., Moldawer N., et al., "Concomitant Administration of Recombinant Human Interleukin–2 and Recombinant Interferon alfa–2A: An Active Outpatient Regimen in Metastatic Renal Cell Carcinoma," *J. Clin. Oncol.*, 10:414–421, 1992.
Sleijfer D. Th., Janssen R. A. J., Buter J., et al., "Phase II Study of Subcutaneous Interleukin–2 in Unselected Patients With Advanced Renal Cell Cancer on an Outpatient Basis," *J. Clin. Oncol.* 10:1119–1123, 1992.
Oren M. E. and Herberman R. B., "Delayed Cutaneous Hypersensitivity Reactions to Membrane Extracts of Human Tumour Cells," *Clin. Exp. Immunol* 9:45–56, 1971.

*Primary Examiner*—Hazel F. Sidberry
*Assistant Examiner*—Julie Krsek-Staples
*Attorney, Agent, or Firm*—Klarquist Sparkman Campbell Leigh & Whinston

[57] ABSTRACT

A breast cancer vaccine which comprises a mixture of tumor associated antigens (TAA) with low doses of recombinant interleukin-2 (IL-2) and granulocyte-macrophage colony stimulating factor (GM-CSF).

3 Claims, 3 Drawing Sheets

CANCER VACCINE FORMULATION 0.1 ml OF TAA PREP

+

0.1ml (CONTAINING ONE MILLION UNITS) OF GM-CSF

+

0.1 ml (CONTAINING 10,000 IU) OF IL-2

VACCINE READY FOR INJECTION

FIGURE 3

PROTOCOL AND PROCESS OF VACCINATION OF CANCER PATIENT

CANCER PATIENT VACCINATION PROCESS:

1. TEST FOR LYMPHOCYTE REACTIVITY TO TAA

2. TREAT WITH CHEMOTHERAPY
   (e.g., cis-platinum-transferrin or do not treat)

3. WAIT 2-3 WEEKS POST-CHEMOTHERAPY

4. POSSIBLY RETEST FOR LYMPHOCYTE REACTIVITY TO TAA

5. VACCINATE WITH VACCINE FORMULATED AS PER FIGURE 2 AT WEEKLY INTERVALS X3

6. INITIATE TREATMENT WITH ORAL IMMUNE STIMULATOR (e.g., PROZAC) AT TIME OF VACCINATION INITIATION

7. RETEST FOR LYMPHOCYTE REACTIVITY TO TAA

8. BOOST WITH VACCINE IF RETEST OF LYMPHOCYTES TO TAA IS NEGATIVE

9. MONITOR FOR CLINICAL STATUS AND CONTINUE TREATING WITH ORAL STIMULATOR (e.g., PROZAC)

VACCINATION OF CANCER PATIENTS USING TUMOR-ASSOCIATED ANTIGENS MIXED WITH INTERLEUKIN-2 AND GRANULOCYTE-MACROPHAGE COLONY STIMULATING FACTOR

BACKGROUND OF THE INVENTION

A number of attempts to vaccinate cancer patients with tumor cells or "tumor-associated antigenic" material obtained from the cells have yielded some positive, but largely equivocal results (1–11). A major limitation of the earlier vaccine studies was that the investigations had no immunological assay available to monitor whether they were, in fact, effectively immunizing the patients against tumor associated antigens TAA with the vaccination procedures used. The Applicants routinely use a lymphocyte-mediated lymphocyte blastogenesis assay (12) with TAA as the stimulant to determine whether the patient has had a sufficient immunological response.

Most of the published studies related to the vaccination of patients against tumors have presented the use of adjuvants such as BCG, DETOX, and viral oncolysates, alum, and complete Freund's adjuvant (1, 3, 5–9, 11) to attempt to enhance immunity against the tumor. Other studies have attempted to use high doses of lymphokine/cytokine agents including interleukin-2 IL-2 (13, 15–18) and granulocyte-macrophage colony stimulating factor GM-CSF (14) to treat patients with various types of cancer, including renal carcinoma (14–18), colorectal and lung carcinoma (16), and melanoma (14). These studies too, have demonstrated negative, or at best weakly positive, results. Varying degrees of toxicity have been associated with the use of extended high doses (one million IU or greater) of IL-2 or GM-CSF therapy, because high dose levels of these agents have been administered to the patients over extended periods of time, ranging from weeks to months. Toxic reactions have included death, renal failure, and many of the WHO Toxicity criteria such as nausea, vomiting, diarrhea, fatigue, depression, and fevers.

There are no published reports of the treatment of cancer patients with a process in which TAA is mixed with low doses (one-tenth as the Applicants do with GM-CSF or one ten-thousandth as the Applicants do with IL-2) of lymphokine/cytokine agents. There is similarly no teaching that the patients may first have undergone intense immunmodulatory chemotherapy one to three weeks prior to vaccination, or that the patient may receive a non-specific lymphocyte stimulator, such as Prozac™ (Hailey, Ward, McCoy, et al.: unpublished results), concurrently with the vaccine. The Applicants of the present invention have combined the use of autologous or allogeneic TAA mixed with low doses of IL-2 and GM-CSF in patients, who have or have not been treated with immunomodulatory (Haily, Ward, McCoy, et al.: unpublished results) and antineoplastic agents (e.g., cisplatin-transferrin, U.S. Pat. No. 4,590,001, Platinum bound to transferrin for use in treatment of breast cancer) within one to three weeks of vaccination and have, also, concurrently been treated with an oral non-specific lymphocyte stimulator (e.g., Prozac™, generically known as fluoxetine).

Tumor cell surface membrane antigen preparations obtained following hypotonic saline extraction (19) have been shown to be antigenic in inducing delayed type hypersensitivity reactions (19) in autologous cancer patients and inducing in vitro lymphocyte mediated immunity (12) using autologous or allogeneic lymphocytes from cancer patients. Thus, the results indicate that human cancers possess TAAs and the cancer-bearing host attempts to elicit a lymphocyte mediated response against the tumor. Recently, the Applicants have reported that breast cancer patients who have demonstrable lymphocyte immunity against TAA are at a very low risk of disease recurrence, suggesting that lymphocyte immunity against TAA is in some ways retarding or eliminating the growth of the tumor in those patients.

Various embodiments of the cancer vaccination process of the present invention take advantage of several factors that the inventors have found to be important in development of an immune response against foreign antigens (such as TAA). These factors include use of GM-CSF to stimulate monocytes that are vital in antigen processing and antigen presentation to lymphocytes; use of IL-2 to stimulate clonal expansion of T-lymphocytes; priming of the patient's immune system prior to vaccination with chemotherapeutic, anti-neoplastic agents, such as cis-Dichlorodiammineplatinum (II) transferrin (cisplatin-transferrin) to stimulate lymphocyte proliferation; and treatment of the patient with an oral lymphocyte proliferative stimulator such as the antidepressant fluoxetine (Prozac™). The combination of these agents and their use in the vaccination process optimizes potential development of lymphocyte immunity against tumor. The administration of the vaccine intradermally into the groin area where inguinal and mesentery lymph node drainage can occur promotes infiltration of lymphocytes and monocytes into the injection site.

SUMMARY OF THE INVENTION

A novel vaccination process has been devised for the immunological treatment of cancer patients. The unique characteristics of this new vaccination process that makes it so attractive are 1) the priming and non-specific stimulation of the lymphocyte system's competence prior to vaccination with an anti-cancer agent, such as cisplatin-transferrin; 2) the recruited and rapid stimulation of monocytes or macrophages by low dose GM-CSF at the vaccination site that also has in its presence TAA, where antigen processing and presentation to lymphocytes can occur; 3) the IL-2 stimulation of TAA sensitized T-lymphocytes at the vaccination site to clonally expand following their sensitization by TAA; 4) the use of an oral non-specific lymphocyte proliferation stimulator concurrently and subsequent to vaccination; 5) the use of the groin area for vaccination where draining lymph nodes from the inguinal and mesenteric areas can infiltrate rapidly; 6) the potential usefulness of the developed lymphocyte immunity against TAA in growth control or eradication of occult or evident metastatic cancer cells; 7) the lack of any toxicity (because of the low dose and only three weekly injections of the IL-2 and GM-CSF that the Applicants use) of GM-CSF and IL-2 that is usually associated with the use of these agents in the treatment of cancer patients; and importantly, 8) the availability of a laboratory test (12) to monitor whether the Applicants have effectively immunized the patient against TAA by the vaccination process.

TAA is prepared from allogeneic or autologous cancer cells using a hypotonic saline extraction procedure to remove the cell membranes containing TAA. These TAA preparations are mixed with a low dose of GM-CFS (generally one million units) and a low does of IL-2 (generally ten thousand IUs) and injected intradermally into the groin area of patients who have usually been pre-treated with the lymphocyte stimulator and the anticancer agent cisplatin-transferrin, and who usually receive the lymphocyte proliferation stimulator Prozac™ orally concurrent with the vaccination.

BRIEF DESCRIPTION OF THE DRAWINGS

FIG. 3 is a protocol of one embodiment of the vaccination method of the present invention.

DETAILED DESCRIPTION OF THE INVENTION

Figure 1:
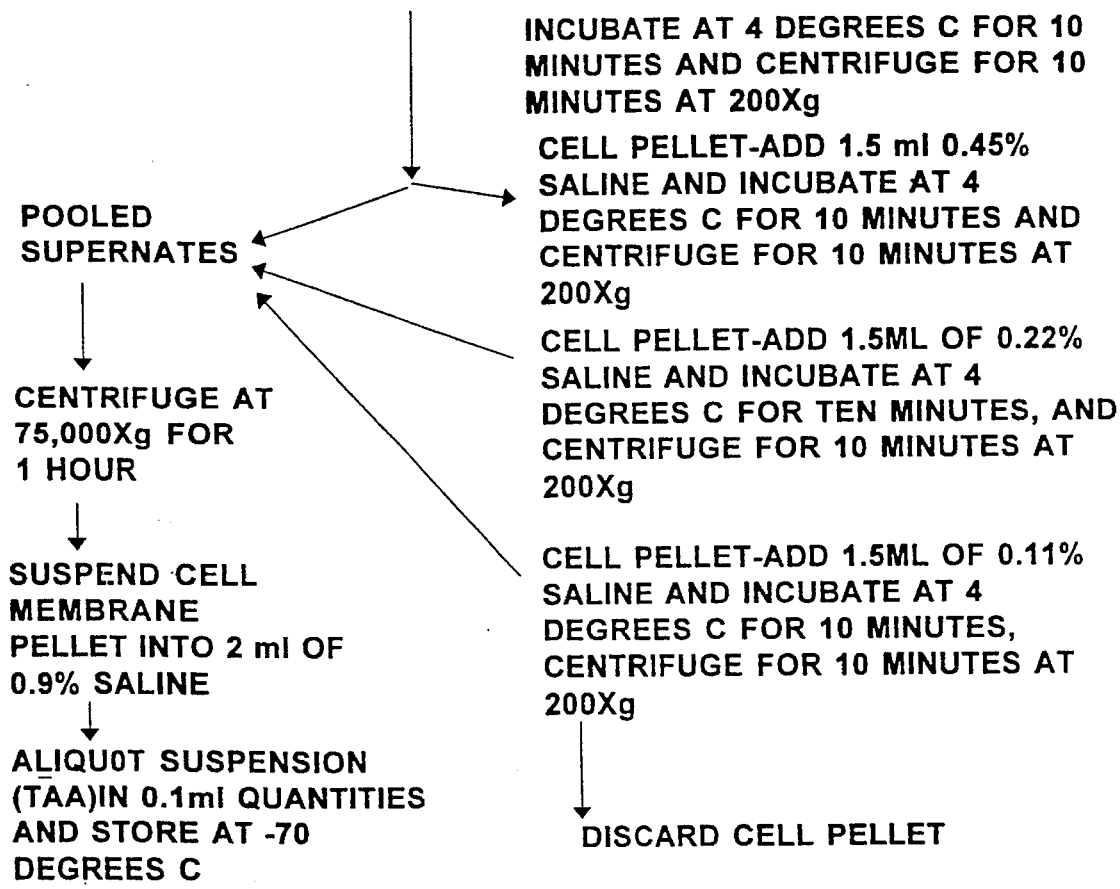
FIG. 1 is a flow diagram illustrating the method of hypotonic extraction of TAA in accordance with the present invention.

The details of the hypotonic extraction preparation of the TAA from cancer cell membranes are presented in FIG. 1. This extraction procedure gently extracts TAA from the cancer cells by carefully reducing the NaCl concentration of the extraction medium from 0.9% (physiological) to 0.11%, leaving cells intact and still containing potential antigen destructive enzymes and other material. The resulting TAA preparation has been shown to be immunologically reactive with autologous lymphocytes from cancer patients in in vitro tests (12) and to induce delayed hypersensitivity skin reactions (19) in autologous and allogeneic cancer patients.

Figure 2:
FIG. 2 illustrates a formulation of an embodiment of the vaccine of the present invention.

The "Vaccine" is usually customized for an individual patient; that is, the autologous or allogeneic TAA is mixed with one million colony forming units of GM-CFS and with ten thousand IUs of IL-2 (see FIG. 2 for details of the formulation of the vaccine). A number of other commercially available cancer antigens can also be used in the "Vaccine" in addition to TAA, including carcinoembryonic antigen (CEA), CA 15-3, CA 125, CA 19-9 and prostrate specific antigen (PSA). The use of these cancer antigens may be used in concert with autologous or allogeneic TAA.

The details of the process of the invention are presented in FIG. 3. In a stepwise fashion, the process is as follows:

1. TAA is prepared as outlined in FIG. 1.
2. Patient lymphocytes are tested for reactivity against autologous or allogeneic TAA, or with the above commercially available antigens by the lymphocyte blastogenesis assay using TAA.
3. The patient is usually treated with an anti-cancer drug (e.g., cisplatin-transferrin, cyclophosphamide, or other chemotherapeutic agent) which can also modulate lymphocyte immunity. Two to three weeks later, the vaccination is initiated.
4. The "Vaccine" is prepared as outlined in FIG. 2. A volume of 0.1 ml of autologous or allogeneic TAA or the commercially available cancer antigens is mixed with GM-CSF (one million colony forming units; obtained commercially from Immunex Corporation, Seattle, Wash., e.g.) or IL-2 (ten thousand IUs; obtained commercially from Cetus Corporation, Emoryville, Calif.).
5. The "Vaccine" is injected intradermally into the groin area of the leg. The vaccination process is repeated at weekly intervals two or more times alternating left and right groin areas with each injection.
6. Simultaneously with vaccination process, the patient also receives an oral immunomodulator such as Prozac™.
7. Patient blood lymphocytes are retested for reactivity against TAA by the lymphocyte blastogenesis assay three weeks after vaccination is completed. If the lymphocyte reactivity against TAA is negative following vaccination, the patient receives three weekly boosters of the "Vaccine" and is retested for lymphocyte reactivity against TAA by the lymphocyte blastogenesis assay.

The laboratory results of testing lymphocyte reactivity against TAA, pre- and post-vaccination, are presented in Table 1.

TABLE 1

LYMPHOCYTE IMMUNITY TO AUTOLOGOUS AND ALLOGENIC BREAST CANCER TAA PRIOR TO AND FOLLOWING VACCINATION[1]

| PATIENT | VACCINATED WITH | LYMPHOCYTE REACTIVITY TO ALLO-TAA OR AUTO-TAA | | | |
|---|---|---|---|---|---|
| | | AUTO-TAA | | ALLO-TAA | |
| | | PRE-VACC. | POST-VACC. | PRE-VACC. | POST VACC. |
| P. B. | ALLO-TAA[2] | | | 1.42 | 4.08 |
| B. F. | AUTO-TAA | 0.95 | 3.13 | | 2.58 |
| E. G. | AUTO-TAA | 1.90 | 2.82 | | 3.10 |
| J. G. | ALLO-TAA | | | 1.28 | 2.11 |
| M. L. | AUTO-TAA | 1.23 | 2.79 | | 2.91 |
| | | | 3.02[3] | | 3.55[3] |
| P. M. | AUTO-TAA | 1.95 | 3.29 | | 2.55 |
| B. N. | AUTO-TAA | 2.20 | 1.77 | | 1.61 |
| | | | 2.10[4] | | 3.50[4] |
| M. S. | AUTO-TAA | 1.47 | 2.11 | | 2.86 |
| | | | 2.26[4] | | 4.42[4] |
| D. W. | AUTO-TAA | 1.15 | 5.53 | | 3.39 |
| T. W. | AUTO-TAA | 0.93 | 1.04 | | 1.81 |

[1] Vaccinations were given intradermally in alternating groin areas weekly X3. Vaccination consisted of (Auto-TAA or Allo-TAA) + IL2 + GM-CSF.
[2] Allo-TAA = allogeneic TAA vaccination; auto-TAA = autologous TAA vaccination.

TABLE 1-continued

LYMPHOCYTE IMMUNITY TO AUTOLOGOUS AND
ALLOGENIC BREAST CANCER TAA PRIOR TO
AND FOLLOWING VACCINATION[1]

| | | LYMPHOCYTE REACTIVITY TO ALLO-TAA OR AUTO-TAA | | | |
|---|---|---|---|---|---|
| | VACCINATED | AUTO-TAA | | ALLO-TAA | |
| PATIENT | WITH | PRE-VACC. | POST-VACC. | PRE-VACC. | POST VACC. |

[3]Two months after third vaccination.
[4]Patient received three booster vaccinations with allo-TAA and was then retested.

A total of ten breast cancer patients received the "Vaccine" (FIG. 2) as per the process outlined in FIG. 3. All but two patients (P.B. and J.G., who received allogeneic TAA) were vaccinated with autologous TAA. No patients had immunity against TAA prior to vaccination. Of the ten patients who had depressed immunity against TAA prior to vaccination, six (60%) developed immunity against breast cancer TAA after the three injections with the "Vaccine." Two of these patients (M.S. and B.N.) received a second series of three injections with allogeneic "Vaccine," and both patients demonstrated increased immunity against allogeneic TAA. Patient M.S., who had already developed immunity against allogeneic TAA, became more reactive to allogeneic TAA, and patient B.N. became reactive to allogeneic TAA. This made a total of eight out of ten (80%) patients who were effectively vaccinated to TAA.

Three of the patients (P.B., M.L., and B.F.) who were negative against TAA initially, and then became positive to TAA following vaccination were advanced in their disease prior to vaccination, so that an objective evaluation of the clinical status pre- and post-vaccination could be made. The results are shown in Table 2.

TABLE 2

CLINICAL STATUS OF BREAST
CANCER PATIENTS PRIOR TO AND
FOLLOWING VACCINATION

| | CLINICAL EVALUATIONS | |
|---|---|---|
| PATIENT | PRE-VACCINATION | POST-VACCINATION |
| P. B. | CAT-SCAN VERIFIED WIDE LIVER METASTASES | SIX WEEKS CAT-SCAN VERIFIED SIGNIFICANT SHRINKAGE OF LIVER METASTATIC LESIONS TWELVE WEEKS CAT-SCAN VERIFIED ADDITIONAL SHRINKAGE OF LIVER METASTATIC LESIONS |
| M. L. | CAT-SCAN VERIFIED LIVER METASTASES | SIX WEEKS CAT-SCAN VERIFIED SIGNIFICANT SHRINKAGE OF LIVER METASTATIC LESIONS TWELVE WEEKS CAT-SCAN VERIFIED ALMOST COMPLETE DISAPPEARANCE OF LIVER METASTASES |
| B. F. | BILATERAL INFLAMMATORY BREAST CANCER | FOUR WEEKS BIOPSY VERIFIED SIGNIFICANT DISEASE REGRESSION |

Both patients, P.B. and M.L., had verified liver metastases of their breast cancers pre-vaccination. There was major regression of these liver lesions in both patients six and twelve weeks post-vaccination as verified by CAT scans. Patient B.F. had extensive local inflammatory breast cancer prior to vaccination. Clinical observation and surgical biopsy four weeks following vaccination showed significant disease regression of her cancer. All of the remaining seven patients who were vaccinated did not have measurable disease; thus, objective clinical changes in these patients cannot yet be observed.

1. Cassel W. A., Murray D. R., Phillips H. S., "A Phase II Study on the Postsurgical Management of Stage II Malignant Melanoma with a Newcastle Disease Virus Oncolysate," Cancer 52:856, 1983.

2. Humphrey L. J., Taschler-Collins S., Goldfarb P. M., et al., "Adjuvant Immunotherapy for Melanoma,"J. Surg. Oncol. 25:303, 1984.

3. Hoover H. C., Surdyke M. G., Dangel R. B., et al., "Prospectively Randomized Trial of Adjuvant Active Specific Immunotherapy for Human Colorectal Cancer," Cancer 55:1236, 1985.

4. Morton D. L., "Adjuvant Immunotherapy of Malignant of Melanoma: Status of Clinical Trials at UCLA," Int. J. Immunotherapy 2:31, 1986.

5. Hersey P., Edwards A., Coates A., et al., "Evidence that Treatment With Vaccinia Melanoma Cell Lysates (VMCL) May Improve Survival of Patients With Stage II Melanoma," Cancer Immunol. Immunotherapy 25:257, 1987.

6. Mitchell M. S., Harel W., Kempf R. A., et al., "Active Specific Immunotherapy for Melanoma," J. Clin. Oncol. 8:856, 1990.

7. Wallack M. K., Bash J., and Bartolucci A., "Improvement in Disease-free Survival of Melanoma Patients in Conjunction With Serologic Response in a Phase Ia/Ib Southeastern Cancer Study Group Trial of Vaccinia Melanoma Oncolysate, " Am Surg. 55:243, 1989.

8. Morton D. L., Nizze A., Famatiga E., et al., "Clinical Results of a Trial of Active Specific Immunotherapy With Melanoma Cell Vaccine and Immunomodulation in Metastatic Melanoma," Proc. Assoc. Cancer Res. 30:383, 1989.

9. Hollinshead A., Stewart T. H. M., Takita H., et al., "Adjuvant Specific Active Lung Cancer Immunotherapy Trials," Cancer, 60:1249, 1987.

10. Wiseman C., Roa S., Kennedy P., et al., "Clinical Responses in Autologous Active Specific Intralymphatic Immunotherapy (AASILI) Correlate With Augmentation of CD4+ Peripheral Blood Lymphocytes (PBL), " Proc. Am. Soc. Clin. Oncol. 8:186, 1989.

11. Livingston P., "Active Specific Immunotherapy in the Treatment of Patients With Cancer," Human Cancer Immunology II:401, 1991.

12. Dean J. H., McCoy J. L., Cannon G. B., et al., "Cell-Mediated Immune Responses of Breast Cancer Patients to Autologous Tumor-Associated Antigens," J.

*National Cancer Inst.* 58:549, 1977.

13. Flaherty L. E., Redman B. G., Chabot G. G., et al., "A Phase I-II Study of Dacarbazine in Combination With Outpatient Interleukin-2 in Metastatic Malignant Melanoma, *Cancer* 65:2471, 1990.

14. Gianni A. M., Bregni M., Siena S., et al., "Recombinant Human Granulocyte-Macrophage Colony-Stimulating Factor Reduces Hematologic Toxicity and Widens Clinical Applicability of High-Dose Cyclophosphamide Treatment in Breast Cancer and Non-Hodgkin's Lymphoma," *J. Clin. Oncol.* 8:768, 1990.

15. Atzpodien J. and Kirchner H., "The Out-Patient Use of Recombinant Human Interleukin-2 and Interferon Alfa-2b in Advanced Malignancies, *Eur. J. Cancer* 27:588, 1991.

16. Caligiuri, M. A., Murray C., Soiffer R. J., et al., "Extended Continuous Infusion Low-Dose Recombinant Interleukin-2 in Advanced Cancer: Prolonged Immunomodulation Without Significant Toxicity," *J, Clin. Oncol.* 9:2110, 1991.

17. Figlin R. A., Belldegrun A., Moldawer N., et al., "Concomitant Administration of Recombinant Human Interleukin-2 and Recombinant Interferon alfa-2A: An Active Outpatient Regimen in Metastatic Renal Cell Carcinoma," *J. Clin. Oncol.* 10:414, 1992.

18. Sleijfer D. Th., Janssen R. A. J., Buter J., et al., "Phase II Study of Subcutaneous Interleukin-2 in Unselected Patients With Advanced Renal Cell Cancer on an Outpatient Basis," *J. Clin. Oncol.* 10:1119, 1992.

19. Oren M. E. and Herberman R. B., "Delayed Cutaneous Hypersensitivity Reactions to Membrane Extracts of Human Tumour Cells," *Clin. Exp. Immunol.* 9:45, 1971.

We claim:

1. A composition comprising 0.1 ml of a suspension containing a human breast cancer tumor associated antigen, one million colony forming units of granulocyte-macrophage colony stimulating factor, and ten thousand international units of interleukin-2.

2. A breast tumor vaccine comprising:

a suspension of a tumor associated antigen from a human breast tumor;

one million colony forming units of granulocyte-macrophage colony stimulating factor; and ten thousand international units of interleukin 2.

3. The breast tumor vaccine of claim 2 wherein the volume of the vaccine is approximately 0.3 ml.

* * * * *